United States Patent
Kamal et al.

(10) Patent No.: US 8,318,726 B2
(45) Date of Patent: Nov. 27, 2012

(54) BENZYLIDINEANTHRACENONE LINKED PYRROLOBENZODIAZEPINE HYBRIDS USEFUL AS ANTICANCER AGENTS AND PROCESS FOR THE PREPARATION THEREOF

(75) Inventors: Ahmed Kamal, Hyderabad (IN); Adla Mallareddy, Hyderabad (IN); Paidakula Suresh, Hyderabad (IN); Rajesh Venkata Chenna Rama Narasimha Chennamshetti, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 34 days.

(21) Appl. No.: 13/048,248

(22) Filed: Mar. 15, 2011

(65) Prior Publication Data

US 2012/0142913 A1    Jun. 7, 2012

(30) Foreign Application Priority Data

Dec. 6, 2010   (IN) ........................... 2886/DEL/2010

(51) Int. Cl.
 *C07D 243/10* (2006.01)
 *A61K 31/5517* (2006.01)
 *A61P 31/00* (2006.01)
(52) U.S. Cl. ........................ 514/220; 540/496
(58) Field of Classification Search .................. 514/220; 540/496
See application file for complete search history.

(56) References Cited

U.S. PATENT DOCUMENTS 7,173,026 B2 * 2/2007 Kamal et al. .................. 514/220
7,465,724 B2 * 12/2008 Kamal et al. .................. 514/220

OTHER PUBLICATIONS

S. Kunimoto, et al; "Mazethramycin, A New Member of Anthramycin Group Antibiotics", The Journal of Antibiotics, vol. 33, No. 6, 1980, pp. 665-667.
Kurt W. Kohn, et al; "Reaction of Anthramycin with Deoxyribonucleic Acid", Journal of Molecular Biology, vol. 51, Issue 3, Aug. 14, 1970, pp. 551-572.
Laurence H. Hurley, et al; "Pyrrolo(1,4)Benzodiazepine Antitumor Antibiotics In Vitro Interaction of Anthramycin, Sibiromycin and Tomaymycin With DNA Using Specifically Radiolabelled Molecules", Biochimica et Biophysica Acta, vol. 475 (1977), pp. 521-535.
David J. Kaplan, et al; "Anthramycin Binding to Deoxyribonucleic Acid-Mitomycin C Complexes. Evidence for Drug-Induced Deoxyribonucleic Acid Conformational Change and Cooperativity in Mitomycin C Binding", Biochemistry, Dec. 22, 1981; vol. 20, Issue 26: pp. 7572-7580.
David E. Thurston, et al; "Synthesis of Sequence-Selective C8-Linked Pyrrolo[2,1-c][1,4]benzodiazepine DNA Interstrand Cross-Linking Agents", The Journal of Organic Chemistry, Nov. 15, 1996; vol. 61, Issue 23, pp. 8141-8147.
Stephen J. Gregson, et al; "Design, Synthesis, and Evaluation of a Novel Pyrrolobenzodiazepine DNA-Interactive Agent with Highly Efficient Cross-Linking Ability and Potent Cytotoxicity", Journal of Medicinal Chemistry; Mar. 1, 2001, vol. 44, Issue 5, pp. 737-748.
Ahmed Kamal, et al; "Design, Synthesis, and Evaluation of New Noncross-Linking Pyrrolobenzodiazepine Dimers with Efficient DMA Binding Ability and Potent Antitumor Activity", Journal of Medicinal Chemistry, Oct. 10, 2002; vol. 45, Issue 21, pp. 4679-4688.
Ahmed Kamal, et al; "Synthesis of Novel C2 and C2-C8 Linked Pyrrolo[2,1-c][1,4]benzodiazepine-naphthalimide Hybrids as DNA-Binding Agents", Bioorganic & Medicinal Chemistry Letters, vol. 13, Issue 20, pp. 3577-3581; Oct. 20, 2003.
Helge Prinz, et al; "Novel Benzylidene-9(10H)-anthracenones as Highly Active Antimicrotubule Agents. Synthesis, Antiproliferative Activity, and Inhibition of Tubulin Polymerization", Journal of Medicinal Chemistry, Jul. 17, 2003; vol. 46, Issue 15, pp. 3382-3394.
Anne Zuse, et al; "9-Benzylidene-naphtho[2,3-b]thiophen-4-ones as Novel Antimicrotubule Agents-Synthesis, Antiproliferative Activity, and Inhibition of Tubulin Polymerization", Journal of Medicinal Chemistry, Dec. 28, 2006; vol. 49, Issue 26, pp. 7816-7825.
David E. Thurston, et al; Synthesis of a novel GC-specific covalent-binding DNA affinity-cleavage agent based on pyrrolobenzodiazepines (PBDs); Chemical Communications; 1996, pp. 563-565.
David E. Thurston, et al; "O-Debenzylation of a Pyrrolo[2,1-c][1,4]benzodiazepine in the Presence of a Carbinolamine Functionality: Synthesis of DC-81", Synthesis, Jan. 1990; pp. 81-84.

* cited by examiner

*Primary Examiner* — Bruck Kifle
(74) *Attorney, Agent, or Firm* — Ladas & Parry LLP

(57) ABSTRACT

The present invention provides a compound of formula 5, useful as potential antitumour agents against human cancer cell lines. The present invention further provides a process for the preparation of pyrrolo[2,1-c][1,4]benzodiazepine hybrids of formula 5a-t.

General formula 5

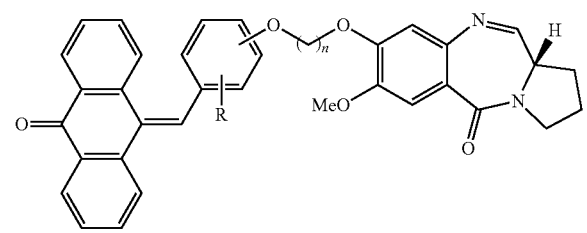

n = 2-6
R = H, alkoxy

19 Claims, 2 Drawing Sheets

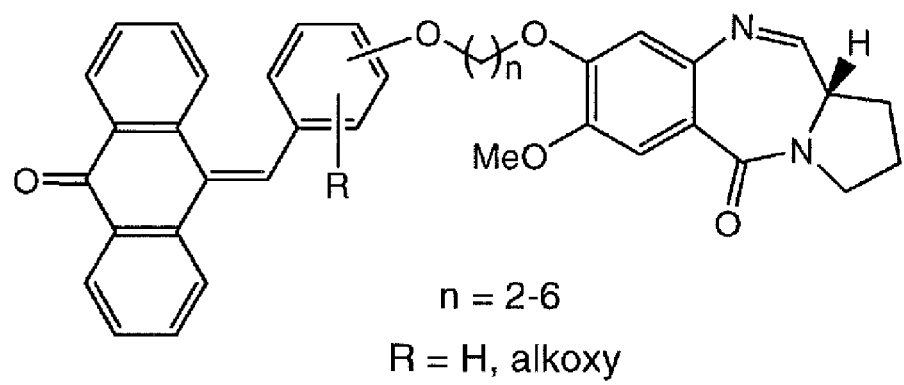
n = 2-6
R = H, alkoxy
5a-t
Scheme-1

US 8,318,726 B2

BENZYLIDINEANTHRACENONE LINKED PYRROLOBENZODIAZEPINE HYBRIDS USEFUL AS ANTICANCER AGENTS AND PROCESS FOR THE PREPARATION THEREOF

FIELD OF THE INVENTION

The present invention relates to benzylidineanthracenone linked pyrrolo[2,1-c][1,4]benzodiazepine hybrids of formula 5 and a process for the preparation thereof.

Formula 5

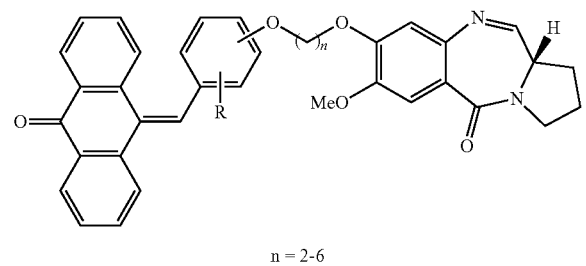

n = 2-6 wherein R═H, OCH$_3$; n=2-6

Present invention further relates to 7-methoxy-8{-substituted-10-(phenoxymethylene)-9,10-dihydro-9-anthracenone)alkyl]oxy}-(11aS)-1,2,3,11a-tetrahydro-5H-pyrrolo[2,1-c][1,4]benzodiazepine-5-one with aliphatic chain length variations useful as anticancer agent.

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

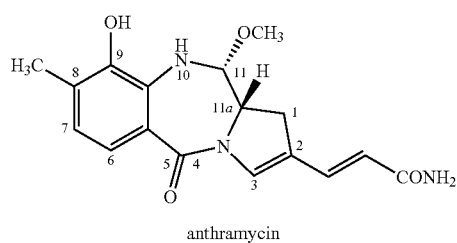

anthramycin

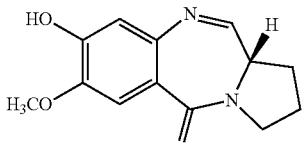

DC-81

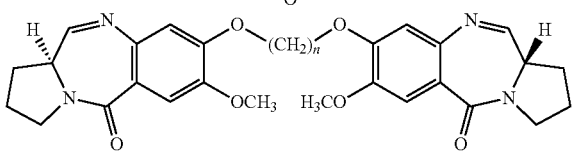

DC-81 dimers (n = 3-5); DSB-120 (n = 3)

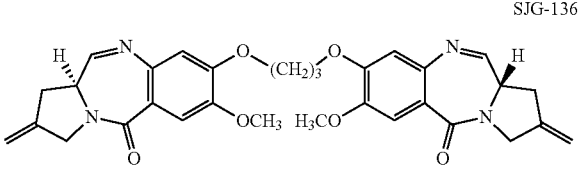

SJG-136

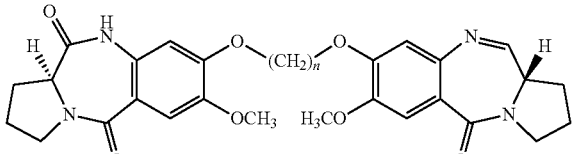

imine-amide PBD dimers; n = 3-5

Recently, PBD dimers have been developed that comprise of two C$_2$-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). Non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity. (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from Streptomyces species. Recently, there is much impetus for the PBD systems as they can recognize and bind to specific sequence of DNA. Examples of naturally occurring PBDs include anthramycin, DC-81, tomaymycin, sibiromycin and neothramycin.

OBJECTIVES OF THE INVENTION

The main objective of the present invention is to provide benzylidine anthracenone linked pyrrolo[2,1-c][1,4]benzodiazepine hybrids of formula 5, useful as antitumour agents.

Yet another object of this invention is to provide a process for the preparation of benzylidine anthracenone linked pyrrolo[2,1-c][1,4]benzodiazepine hybrids of formula 5.

SUMMARY OF THE INVENTION

Accordingly, present invention provides benzylidineanthracenones linked pyrrolo[2,1-c][1,4]benzodiazepine hybrids of formula 5 formula 5

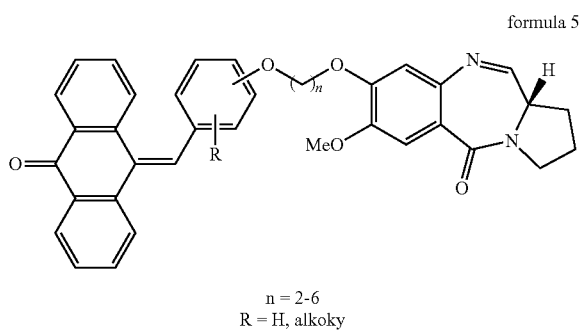

n = 2-6
R = H, alkoky wherein R=H, OCH₃; n=2-6 and the representative compounds are Formula 5 a-e

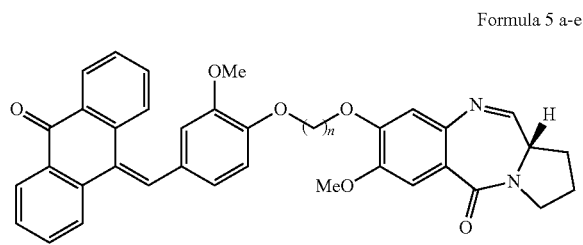

n = 2-6

Formula 5 f-j

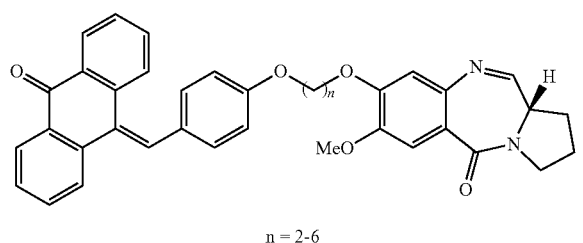

n = 2-6

Formula 5 k-o

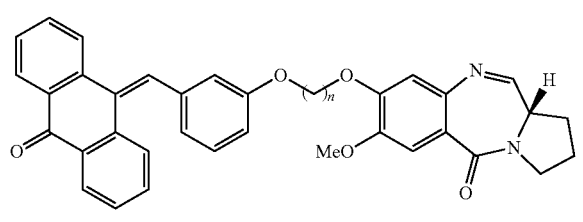

n = 2-6

Formula 5 p-t

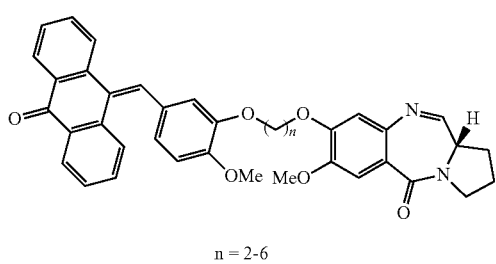

n = 2-6

In an embodiment of the present invention, chemical formula of the representative compounds are:

7-methoxy-8-(2-{2-methoxy-4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5a);

7-methoxy-8-(3-{2-methoxy-4-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5b);

7-methoxy-8-(4-{2-methoxy-4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5c);

7-methoxy-8-(5-{2-methoxy-4-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one (5d);

7-methoxy-8-(6-{2-methoxy-4-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5e);

7-methoxy-8-(2-{4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5f);

7-methoxy-8-(3-{4-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5g);

7-methoxy-8-(4-{4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5h);

7-methoxy-8-(5-{4-[(10-oxo-9,10-dihydro-9-anthracenyliden)methyl]phenoxy} pentoxy)-(11aS)-1,2,3,11a-5H-pyrrolo[2,1-c][1,4]benzodiazepin-5-one (5i);

7-methoxy-8-(6-{4-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5j);

7-methoxy-8-(2-{3-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5k);

7-methoxy-8-(3-{3-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5l);

7-methoxy-8-(4-{3-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5m);

7-methoxy-8-(5-{3-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one (5n);

7-methoxy-8-(6-{3-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5o);

7-methoxy-8-(2-{2-methoxy-5-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5p);

7-methoxy-8-(3-{2-methoxy-5-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5q);

7-methoxy-8-(4-{2-methoxy-5-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5r);

7-methoxy-8-(5-{2-methoxy-5-[(10-oxo-9,10-dihydro-9-anthracenyliden)methyl]phenoxy}pentoxy)(11aS)-1,2,3,11a-5H-pyrrolo[2,1-c][1,4]benzodiazepin-5-one (5s);

7-methoxy-8-(6-{2-methoxy-5-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5t);

In yet another embodiment of the present invention, structural formula of the representative compounds are:
5a
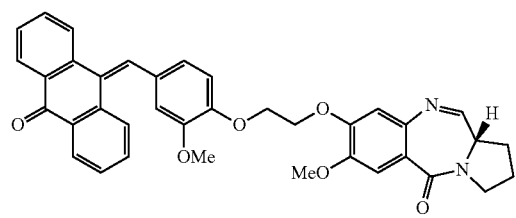
5b
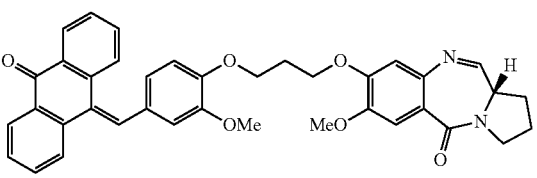
5c
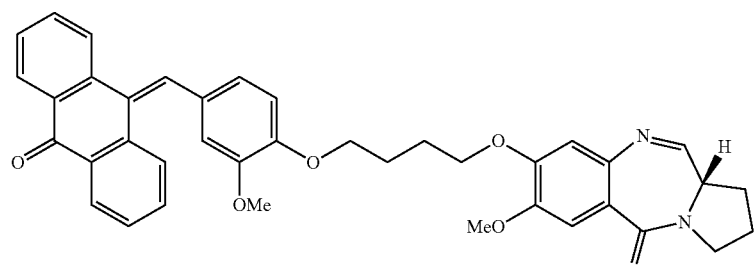
5d
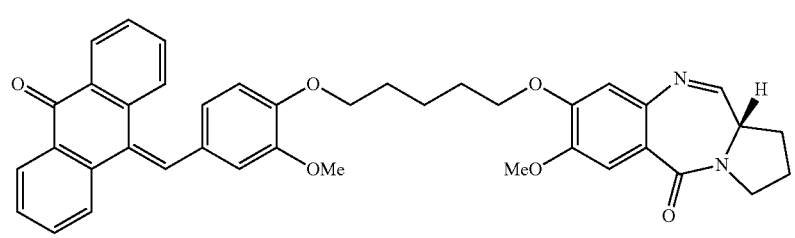
5e
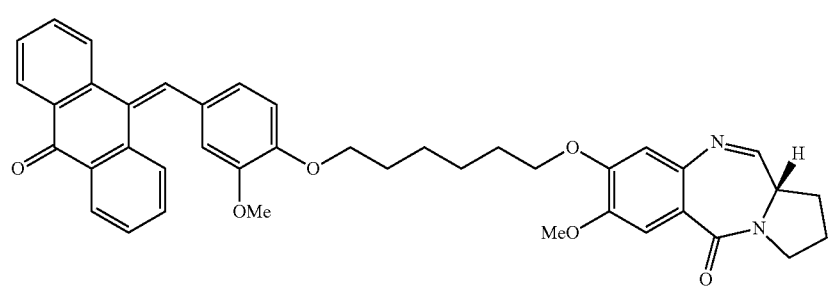
5f
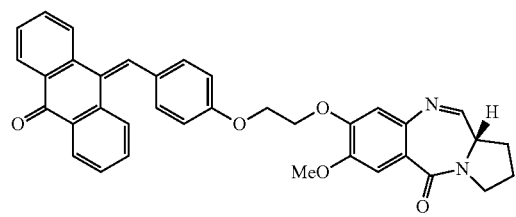
5g
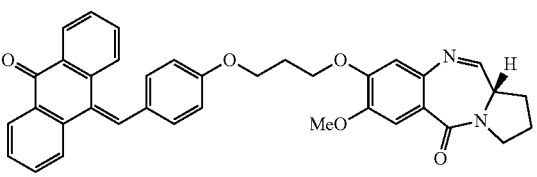
5h
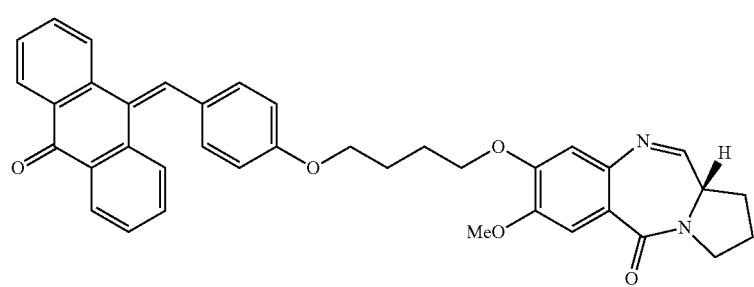

-continued
5i
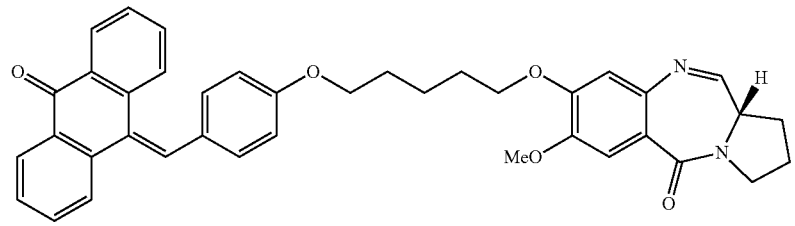
5j
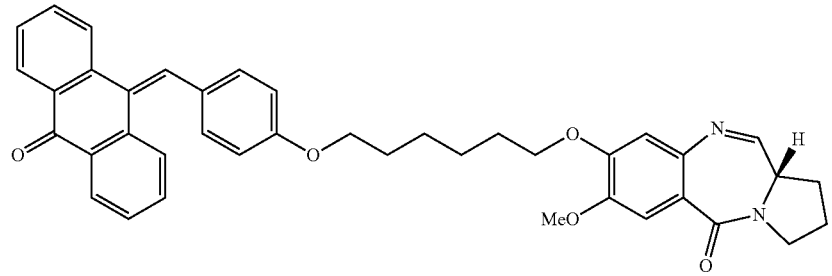
5k
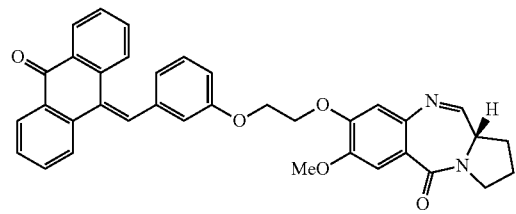
5l
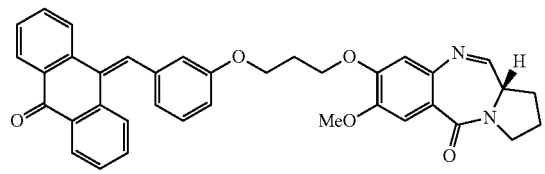
5m
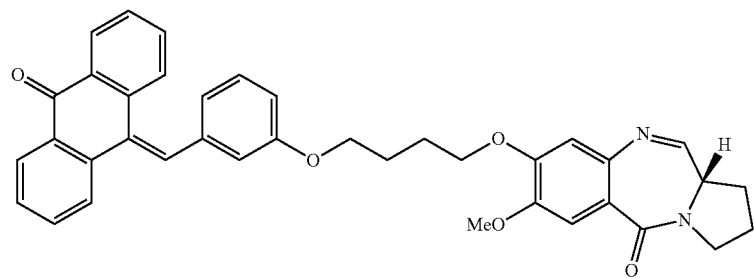
5n
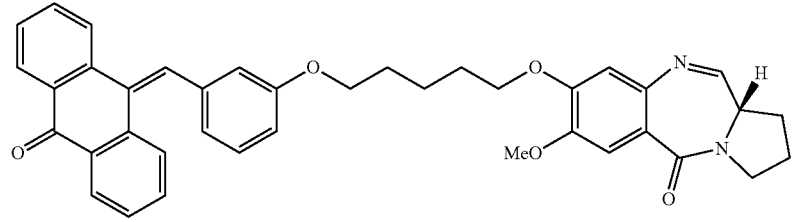
5o
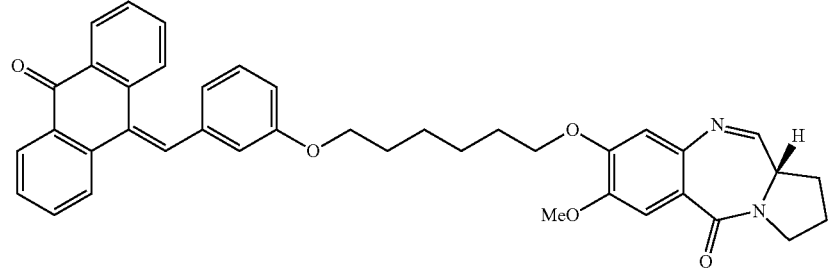

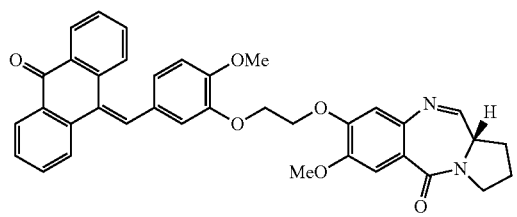
5p

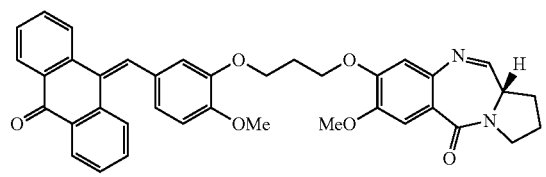
5q

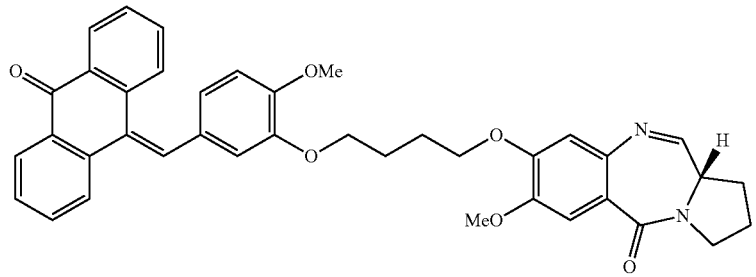
5r

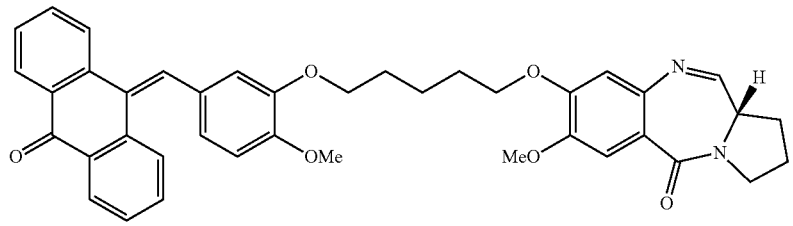
5s

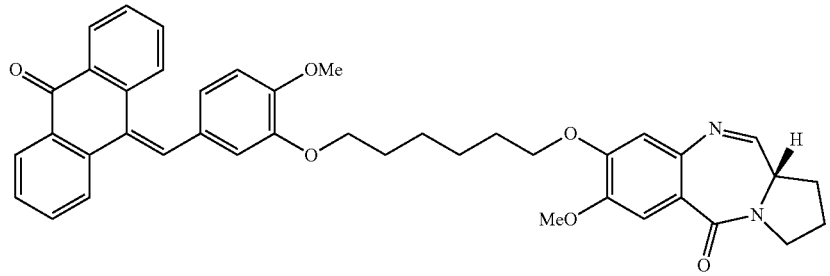
5t

In yet another embodiment of the present invention, said compounds are useful as anticancer agents.

In yet another embodiment of the present invention, a process for the preparation of benzylidineanthracenone linked pyrrolo[2,1-c][1,4]benzo-diazepine hybrid of formula 5 and the process comprising the steps of:

a) reacting (2S)—N-[4-(n-bromoalkyl)oxy-5-methoxy-2-nitrobenzoyl]pyrrolidine-2-carboxaldehyde diethylthioacetal of formula 1a-e;

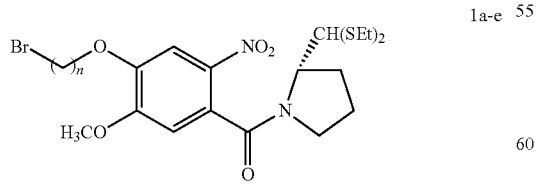

1a n = 2
1b n = 3
1c n = 4
1d n = 5
1e n = 6 with hydroxy substituted benzylidineanthracenone derivative selected from the compound of formula 2a-d

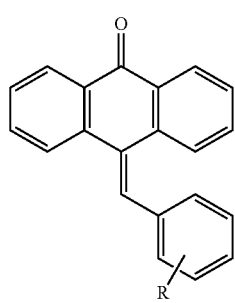
2a-d

2a R = 3-OMe, 4-OH
2b R = 4-OH
2c R = 3-OH
2d R = 4-OMe, 3-OH in the presence of inorganic base, in an organic solvent, at a temperature in the range of 55 to 60° C. to obtain the resultant nitro compound of formula 3a-t;

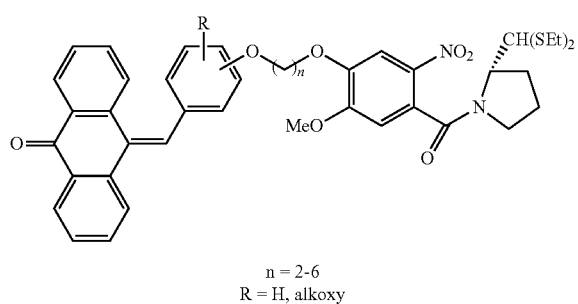

3a-t n = 2-6
R = H, alkoxy b) reducing the compounds of formula 3a-t with $SnCl_2.2H_2O$, in an alcohol, under reflux, followed by the evaporation of alcohol and basifying with a base, followed by extraction with ethyl acetate and washing the combined organic phase with brine solution and evaporating the solvent to obtain the desired amino product of formula 4a-t;

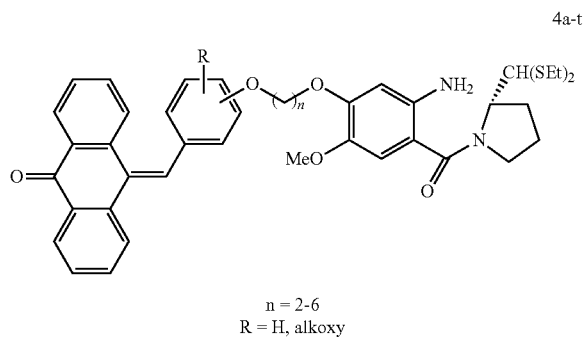

4a-t n = 2-6
R = H, alkoxy c) reacting the above said amino compounds of formulae 4a-t with deprotecting agent, mercuric chloride, in a mixture of water and organic solvent, in the presence of base, under stirring at a temperature in the range of 20-30° C., for a period in the range of 8-12 hrs, followed by filtration, extraction and washing with sodium bicarbonate and brine solution respectively;
d) evaporating the organic layer under reduced pressure;
e) purifying by column chromatography to obtain the desired product of formula 5.

In yet another embodiment of the present invention, the inorganic base used in step (a) is selected from potassium carbonate or sodium carbonate.

In yet another embodiment of the present invention, the organic solvent used in step (a) is selected from the group consisting of acetone, N,N-dimethylformamide and acetonitrile.

In yet another embodiment of the present invention, alcohol used in step (b) is selected from the group consisting of methanol, ethanol and isopropanol.

In yet another embodiment of the present invention, the base used in step (b) is sodium carbonate.

In yet another embodiment of the present invention, the base used in step (c) is calcium carbonate.

In yet another embodiment of the present invention, the organic solvent used in step (c) is selected from the group consisting of acetone, acetonitrile, chloroform, dichloromethane and tetrahydrofuran.

In yet another embodiment of the present invention, Benzylidineanthracenone linked pyrrolo[2,1-c][1,4]benzodiazepine hybrids of formula 5 exhibi an in vitro anticancer activity against human cancer cell lines selected from the group consisting of breast, ovarian, colon, prostate, cervix, lung and oral cancer cell lines.

In still another embodiment of the present invention, the benzylidineanthracenone linked pyrrolo[2,1-c][1,4]benzodiazepine hybrid of formula 5a-o exhibits an in vitro anticancer/antitumour activity against human cancer cell lines selected from the group consisting of lung, cervix, breast, colon, prostate and oral cell lines.

In still another embodiment of the present invention, the concentration of the compound Benzylidineanthracenone linked pyrrolo[2,1-c][1,4]benzodiazepine hybrids 5b, 5c, 5h, 5m, 5r, used for in vitro activity against colon cancer cell lines (Colo205) for $GI_{50}$ is in the range of 0.11 to 0.14 μm at an exposure period of at least 48 hrs.

In still another embodiment of the present invention, the concentration of the compound 5b, 5c, 5d, 5h, 5m, 5r used for in vitro activity against lung cancer cell lines (HoP62) for $GI_{50}$ is in the range of 0.17-0.26 μm at an exposure period of at least 48 hrs.

In still another embodiment of the present invention, the concentration of the compound 5b, 5c, 5d, 5h, 5m, 5r used for in vitro activity against breast cancer cell lines (MCF7) for $GI_{50}$ is in the range of 0.09-0.18 μm at an exposure period of at least 48 hrs.

In still another embodiment of the present invention, the concentration of the compound 5b, 5c, 5d, 5h, 5m, 5r used for in vitro activity against prostate cancer cell lines (PC3) for $GI_{50}$ is in the range of 0.15-2.2 μm at an exposure period of at least 48 hrs.

In still another embodiment of the present invention, the concentration of the compound 5b, 5d, 5h, 5m, 5r, used for in vitro activity against cervix cancer cell lines (SiHa) for $GI_{50}$ is in the range of 2.2-31 μm at an exposure period of at least 48 hrs.

In still another embodiment of the present invention, the concentration of the compound 5b, 5c, 5d, 5h, 5m, 5r used for in vitro activity against ovarian cancer cell lines (A2780) for $GI_{50}$ is in the range of 0.148-0.168 μm at an exposure period of at least 48 hrs.

In still another embodiment of the present invention, the concentration of the compound 5b, 5c, 5d, 5h, 5m, 5r used for in vitro activity against lung cancer cell lines (A549) for $GI_{50}$ is in the range of 0.155-1.94 μm at an exposure period of at least 48 hrs.

In still another embodiment of the present invention, the concentration of the compound 5b, 5c, 5d, 5h, 5m, 5r used for in vitro activity against oral cancer cell lines (KB) for $GI_{50}$ is in the range of 0.18-2.5 μm at an exposure period of at least 48 hrs.

DETAILED DESCRIPTION OF THE INVENTION

Figure 1:
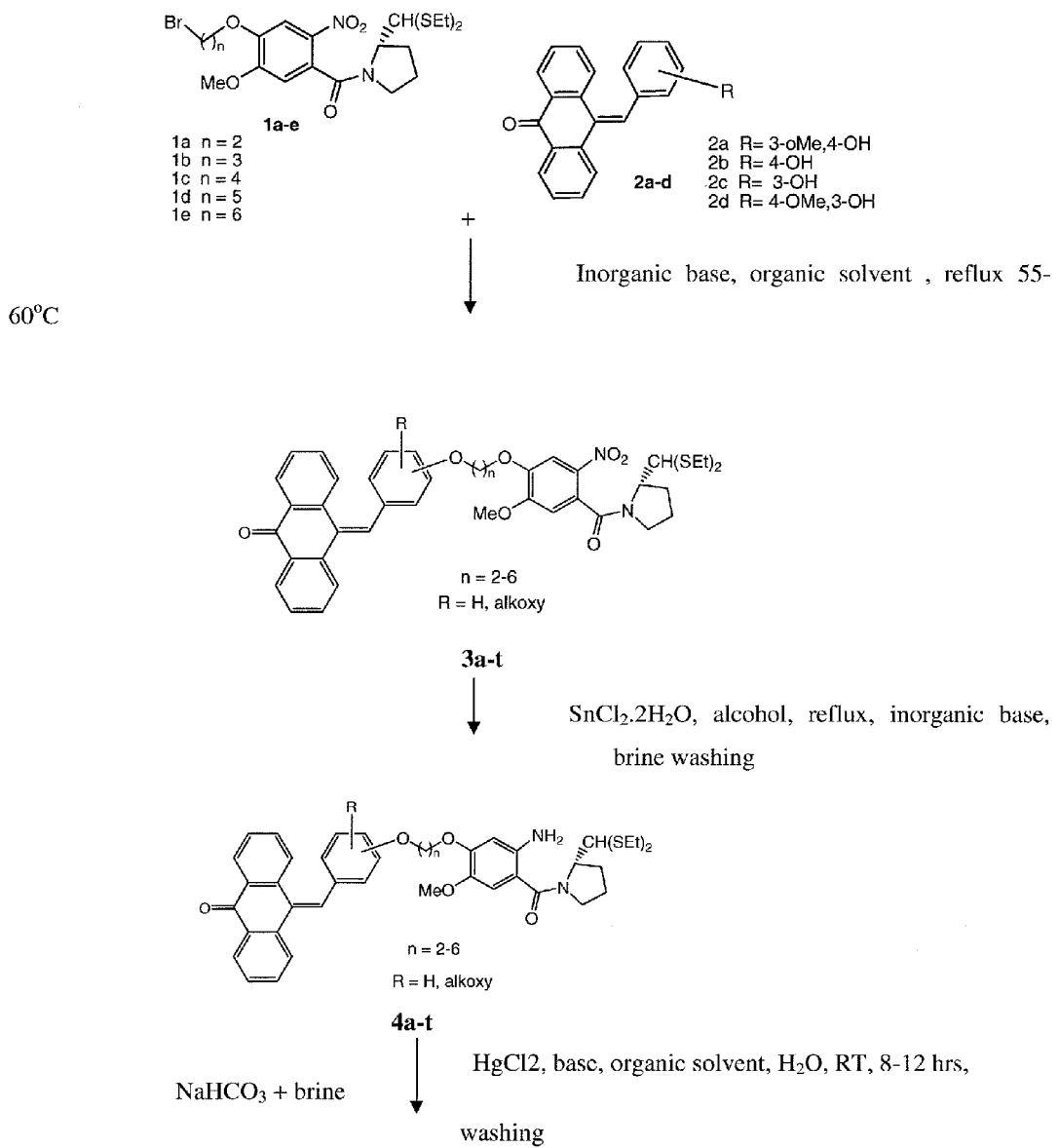
FIG. 1 represents the flow diagram for the preparation of compounds of formula 5 as Scheme 1.

Present invention relates to pyrrolo[2,1-c][1,4]benzodiazepine hybrids of formula 5 and process for preparation of pyrrolo[2,1-c][1,4]benzodiazepine hybrids of formula 5 which comprises reacting hydroxy benzylidineanthracenone of formula 2a-d with (2S)—N-[(n-bromoalkyloxy)-3-methoxy-2-nitrobenzoyl)]pyrrolidine-2-carboxaldehydediethylthioacetal of formula 1a-e in presence of organic solvent and inorganic base with isolating (2S)—N-{3-[substituted or un-substituted benzylidineanthracenone]alkoxy-5-methoxy-2-nitrobenzoyl}pyrrolidi-ne-2-carboxaldehyde diethylthioacetal of formula 3a-t. Further step involves reducing the above nitro compound of formula 3a-t with $SnCl_2.2H_2O$ in presence of alcohol with reflux temperature, resulting with the formation of (2S)—N-{3-[substituted or un-substituted benzylidineanthracenone]alkoxy-5-methoxy-2-aminobenzoyl}pyrrolidi-ne-2-carboxaldehydediethylthioacetal 4a-t. Subsequent step involves reacting the above said amino compound of formula 4a-t with deprotecting agents in a conventional manner to give novel pyrrolo[2,1-c][1,4]benzodiazepine hybrids of formula 5a-t, wherein n is 2-6.

The precursors, substituted hydroxy benzylidineanthracenones of formula 2a-d (*J. Med. Chem.* 2003, 46, 3382-3394, *J. Med. Chem.* 2006, 49, 7816-7825). and (2S)—N-(4-hydroxy-5-methoxy-2-nitrobenzoyl)pyrrolidine-2-carboxaldehydediethylthioacetal of formula 1a-e (Thurston, D. E.; Morris, S. J.; Hartley, J. A. *Chem. Commun.* 1996, 563-565; Thurston, D. E.; Murthy, V. S.; Langley, D. R.; Jones, G. B. *Synthesis*. 1990, 81) have been prepared by literature methods.

Some representative compounds of formula 5 for the present inventions are given below 7-methoxy-8-(3-{2-methoxy-4-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5b);

7-methoxy-8-(4-{2-methoxy-4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5c);

7-methoxy-8-(5-{2-methoxy-4-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one (5d);

7-methoxy-8-(4-{4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5h);

7-methoxy-8-(4-{3-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5m);

7-methoxy-8-(4-{2-methoxy-5-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5r)

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property.

EXAMPLES

The following examples are given by way of illustration and therefore should not be construed to the present limit scope of the invention.

Example-1

(7-Methoxy-8-(3-{2-methoxy-4-[(10-oxo-9,10-dihydro-9-anthracenyliden)methyl]phenoxy} propoxy)-(11aS)-1,2,3,11a-5H-pyrrolo[2,1-c][1,4]benzodiazepin-5-one (5b)

To a solution of 25-N-[4-(3-bromopropoxy)-5-methoxy-2-nitrobenzoyl]pyrrolidine-2-carboxaldehydediethylthioacetal (1b) (521 mg, 1.0 mmol) in dry acetone (20 mL) was added anhydrous potassium carbonate (276 mg, 2.0 mmol) and 4-hydroxy-3-methoxybenzylidineanthracenone (2a) (328 mg, 1.0 mmol). The reaction mixture was refluxed in an oil bath at 57° C. for 24 h and the reaction was monitored by TLC using ethyl acetate-hexane (1:1) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product (3b) (614 mg, 80% yield).

$^1$H NMR (CDCl$_3$): δ 8.18-8.27 (m, 2H), 7.95 (d, 1H, J=8.0 Hz), 7.70 (s, 1H), 7.53-7.65 (m, 2H), 7.32-7.49 (m, 3H), 7.21-7.32 (m, 1H), 6.72-6.88 (m, 4H), 4.80 (d, 1H, J=3.6 Hz), 4.58-4.73 (m, 1H), 4.33 (t, 2H, J=5.8 Hz), 4.22 (t, 2H, J=5.8 Hz), 3.92 (s, 3H), 3.64 (s, 3H), 3.14-3.26 (m, 2H), 2.63-2.86 (m, 4H), 2.29-2.47 (m, 2H), 2.02-2.29 (m, 2H), 1.73-1.98 (m, 2H), 1.25-1.40 (m, 6H). ESI-MS: 769 (M+1)$^+$.

To a compound of 3b (768 mg, 1.0 mmol) in methanol (10 mL), SnCl$_2$.2H$_2$O (1.125 g, 5.0 mmol) was added and refluxed until the TLC indicated the completion of the reaction. The methanol was then evaporated in vacuum and basified with 10% NaHCO$_3$ solution and extracted with ethylacetatate (2×60 mL). The combined organic phase was dried over Na$_2$SO$_4$ and evaporated under vacuum to afford the crude aminodiethylthioacetal 4b (642 mg, 95% yield), which was directly used in the next step.

A solution of 4b (738 mg, 1.0 mmol), HgCl$_2$ (544 mg, 2.0 mmol) and CaCO$_3$ (200 mg, 2.0 mmol) in acetonitrile-water was stirred slowly at 27° C. until complete consumption of starting material as indicated by the TLC. The reaction mixture was filtered to separate the salts and the filtrate was extracted with ethyl acetate. The ethylacetate layer was washed with saturated 5% NaHCO$_3$ (50 mL) followed by brine solution (50 mL) and the organic phase was dried over Na$_2$SO$_4$. The organic layer was evaporated in vacuum to afford crude product, which was purified by column chromatography with ethyl acetate and hexane as eluaent to obtain the pure product 5b (312 mg, 52% yield).

$^1$H NMR (CDCl$_3$): δ 8.28-8.19 (m, 2H), 7.99 (d, 1H), 7.68-7.56 (m, 3H), 7.52-7.34 (m, 4H), 7.24-7.32 (m, 1H), 6.74-6.92 (m, 4H), 4.16-4.43 (m, 4H), 3.93 (s, 3H), 3.86-3.80 (m, 1H), 3.7-3.84 (m, 2H), 3.59-3.67 (m, 4H), 2.24-2.46 (m, 2H), 1.94-2.21 (m, 4H), ESI-MS: 615 (M+1)$^+$.

Example-2

(7-Methoxy-8-(4-{2-methoxy-4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5c);

The compound 3c has been prepared according to the method described for the compound 3b by employing the compounds 1c (535 mg, 1.0 mmol), anhydrous K$_2$CO$_3$ (276 mg, 2.0 mmol) and compound (2a) (328 mg, 1.0 mmol) to afford the compound 3c (625 mg, 80%).

$^1$H NMR (CDCl$_3$): δ 8.23-8.30 (m, 2H), 8.02 (d, 1H, J=8.1 Hz), 7.69 (s, 1H), 7.60-7.68 (m, 2H), 7.45-7.54 (m, 2H), 7.38-7.44 (t, 1H, J=6.7 Hz), 7.26-7.31 (m, 1H), 6.90-6.94 (m, 1H), 6.80-6.86 (m, 3H), 4.88 (d, 1H, J=3.7 Hz), 4.67-4.75 (m, 1H), 4.22 (t, 2H, J=5.8 Hz), 4.14 (t, 2H, J=5.8 Hz), 3.92 (s, 3H), 3.65 (s, 3H), 3.20-3.32 (m, 2H), 2.68-2.87 (m, 4H), 2.21-2.34 (m, 1H), 2.05-2.15 (m, 5H), 1.90-2.02 (m, 1H), 1.74-1.86 (m, 1H), 1.29-1.39 (m, 6H). ESI-MS: 783 (M+1)$^+$.

The compound 4c has been prepared according to the method described for the compound 4b by reducing compound 3c (782 mg, 10 mmol) using $SnCl_2.2H_2O$ (1.125 g, 5.0 mmol) to afford compound 4c (740 mg, 95%), which was directly used in the next step The compound 5c was prepared according to the method described for the compound 5b employing the compound 4c (752 mg, 10 mmol) and $HgCl_2$ (544 mg, 2.00 mmol), $CaCO_3$ (200 mg, 2.46 mmol) to afford the compound 5b (314 mg, 50% yield).

$^1$H NMR ($CDCl_3$): δ 8.21-8.26 (m, 2H), 7.96 (d, 1H, J=8.3 Hz), 7.55-7.66 (m, 3H), 7.34-7.48 (m, 4H), 7.23-7.31 (m, 1H), 6.83-6.90 (m, 1H), 6.74-6.80 (m, 3H), 4.06-4.13 (m, 4H), 3.92 (s, 3H), 3.76-3.86 (m, 1H), 3.66-3.71 (m, 1H), 3.62 (s, 3H), 3.52-3.58 (m, 1H), 2.27-2.36 (m, 2H), 1.98-2.14 (m, 6H), ESI-MS: 629 (M+1)$^+$.

Example-3

7-Methoxy-8-(5-{2-methoxy-4-[(10-oxo-9,10-dihydro-9-anthracenyliden)methyl]phen-oxy}pentoxy)-(11aS)-1,2,3,11a-5H-pyrrolo[2,1-c][1,4]benzodiazepin-5-one (5d);

The compound 3d has been prepared according to the method described for the compound 3b by employing the compounds 1d (549 mg, 10 mmol), anhydrous $K_2CO_3$ (276 mg, 20 mmol) and compound (2a) (328 mg, 1.0 mmol) to afford the compound 3d (636 mg, 82%).

$^1$H NMR ($CDCl_3$): δ 8.21-8.26 (m, 2H), 7.96 (d, 1H, J=8.3 Hz), 7.57-7.65 (m, 3H), 7.37-7.48 (m, 3H), 7.23-7.28 (m, 1H), 6.85-6.91 (m, 1H), 6.76-6.78 (m, 3H), 4.81 (d, 1H, J=3.7 Hz), 4.63-4.69 (m, 1H), 4.02-4.14 (m, 4H), 3.93 (s, 3H), 3.64 (s, 3H), 3.16-3.30 (m, 2H), 2.63-2.87 (m, 4H), 2.16-2.38 (m, 2H), 1.87-2.14 (m, 5H), 1.68-1.87 (m, 3H), 1.28-1.39 (m, 6H), ESI-MS: 797 (M+1)$^+$.

The compound 4d has been prepared according to the method described for the compound 4b by reducing compound 3d (796 mg, 1.0 mmol) using $SnCl_2.2H_2O$ (1.125 g, 5.0 mmol) to afford compound 4d (640 mg, 95%), which was directly used in the next step.

The compound 5d was prepared according to the method described for the compound 5b employing the compound 4d (766 mg, 1.0 mmol) and $HgCl_2$ (544 mg, 2.0 mmol), $CaCO_3$ (200 mg, 2.0 mmol) to afford the compound 5d (430 mg, 67% yield).

$^1$H NMR ($CDCl_3$): δ 8.29-8.19 (m, 2H), 7.98 (d, 1H, J=8.1 Hz), 7.69-7.55 (m, 3H), 7.51-7.31 (m, 4H), 7.31-7.21 (m, 1H), 6.94-6.83 (m, 1H), 6.8-6.71 (m, 3H), 3.98-4.10 (m, 4H), 3.93 (s, 3H), 3.86-3.76 (m, 1H), 3.7-3.74 (m, 1H), 3.54-3.68 (m, 4H), 2.23-2.4 (m, 2H), 1.82-2.14 (m, 6H), 1.21-1.29 (m, 2H) ESI-MS: 643 (M+1)$^+$.

Example-4

7-Methoxy-8-(4-{4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5h)

The compound 3h has been prepared according to the method described for the compound 3b by employing compounds 1c (521 mg, 1.0 mmol), anhydrous $K_2CO_3$ (276 mg, 2.0 mmol) and compound (2b) (298 mg, 1.0 mmol) to afford the compound 3h (676 mg, 90%).

$^1$H NMR ($CDCl_3$): δ 8.19-8.27 (m, 2H), 7.95 (d, 1H, J=7.3 Hz), 7.53-7.66 (m, 3H), 7.35-7.48 (m, 2H), 7.19-7.30 (m, 4H), 6.76-6.80 (m,3H), 4.81 (d, 1H, J=3.6 Hz), 4.59-4.71 (m, 1H), 4.17 (t, 2H, J, 5.1 Hz), 4.07 (t, 2H, J=5.1 Hz), 3.91 (s, 3H), 3.16-3.29 (m, 2H), 2.67-2.85 (m, 4H), 2.19-2.35 (m, 1H), 1.90-2.15 (m, 6H), 1.72-1.90 (m, 1H), 1.26-1.40 (m, 6H).

ESI-MS: 753 (M+1)$^+$.

The compound 4h has been prepared according to the method described for the compound 4b by reducing compound 3h (752 mg, 10 mmol) using $SnCl_2.2H_2O$ (1.125 g, 5.0 mmol) to afford compound 4h (715 mg, 95%), which was directly used in the next step.

The compound 5h was prepared according to the method described for the compound 5b employing the compound 4h (722 mg, 1.0 mmol) and $HgCl_2$ (544 mg, 2.0 mmol), $CaCO_3$ (200 mg, 2.0 mmol) to afford the compound 5h (358 mg, 67% yield).

$^1$H NMR ($CDCl_3$): δ 8.29-8.19 (m, 2H), 7.97 (d, 1H, J=8.3 Hz), 7.65-7.57 (m, 3H), 7.53-7.35 (m, 4H), 7.17-7.25 (m, 3H), 6.83-6.75 (m, 3H), 4.14-3.99 (m, 4H), 3.82 (s, 3H), 3.69-3.75 (m, 1H), 3.45-3.63 (m, 1H), 3.37-3.23 (m, 1H), 2.24-2.36 (m, 2H), 1.93-2.17 (m, 6H) ESI-MS: 599 (M+1)$^+$.

Example-5

7-Methoxy-8-(4-{3-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5m);

The compound 3m has been prepared according to the method described for the compound 3b by employing the compounds 1c (521 mg, 1.0 mmol), anhydrous $K_2CO_3$ (276 mg, 2.0 mmol) and compound (2c) (298 mg, 1.0 mmol) to afford the compound 3m (662 mg, 87%).

$^1$H NMR ($CDCl_3$): δ 8.19-8.26 (m, 2H), 7.97 (d, 1H, J=7.5 Hz), 7.59-7.66 (m, 2H), 7.45-7.50 (m, 3H), 7.38 (t, 1H, J=6.7, 8.3 Hz), 7.16-7.23 (m, 2H), 6.85 (d, 1H, J=7.5 Hz), 6.76-6.79 (m, 3H), 4.81 (d, 1H, J=3.7 Hz), 4.63-4.69 (m, 1H), 4.14 (t, 2H, J=5.2 Hz), 3.91-3.95 (m, 5H), 3.17-3.30 (m, 2H), 2.66-2.84 (m, 4H), 2.21-2.33 (m, 1H), 1.95-2.15 (m, 6H), 1.73-1.87 (m, 1H), 1.31-1.39 (m, 6H). ESI-MS: 753 (M+1)$^+$.

The compound 4m has been prepared according to the method described for the compound 4b by reducing compound 3m (752 mg, 10 mmol) using $SnCl_2.2H_2O$ (1.12 g, 5.0 mmol) to afford compound 4m (710 mg, 93%), which was directly used in the next step.

The compound 5m was prepared according to the method described for the compound 5b employing the compound 4m (722 mg, 1.0 mmol) and $HgCl_2$ (544 mg, 2.00 mmol), $CaCO_3$ (200 mg, 2.0 mmol) to afford the compound 5m (359 mg, 68% yield).

$^1$H NMR ($CDCl_3$): δ 8.22-8.30 (m, 2H), 8.02 (d, 1H, J=7.5 Hz), 7.62-7.67 (m, 2H), 7.48-7.55 (m, 4H), 7.39 (t, 1H, J=7.5 Hz), 7.11-7.27 (m, 3H), 6.74-6.91 (m, 4H), 4.04-4.19 (m, 4H), 3.93 (s, 3H), 3.77-3.86 (m, 1H), 3.69-3.74 (m, 1H), 3.53-3.63 (m, 1H), 2.24-2.37 (m, 2H), 1.85-2.14 (m, 6H). ESI-MS: 599 (M+1)$^+$.

Example-6

7-Methoxy-8-(4-{2-methoxy-5-[(10-oxo-9,10-dihydro-9-anthracenyliden)methyl]-phenoxy}butoxy)-(11aS)-1,2,3,11a-5H-pyrrolo[2,1-c][1,4]benzodiazepin-5-one (5r)

The compound 3r has been prepared according to the method described for the compound 3b by employing the compounds 1c (535 mg, 1.0 mmol), anhydrous $K_2CO_3$ (276 mg, 2.0 mmol) and compound (2d) (328 mg, 1.0 mmol) to afford the compound 3r (703 mg, 90%).

$^1$H NMR (CDCl$_3$): δ 8.19-8.30 (m, 2H), 8.0 (d, 1H, J=7.9 Hz), 7.58-7.70 (m, 3H), 7.43-7.53 (m, 2H), 7.39 (t, 1H, J=6.93 Hz), 7.23-7.30 (m, 1H), 6.89-6.96 (m, 1H), 6.77-6.86 (m, 3H), 4.85 (d, 1H, J=3.5 Hz), 4.66-4.74 (m, 1H), 4.11-4.23 (m, 4H), 3.91 (s, 3H), 3.87 (s, 3H), 3.19-3.33 (m, 2H), 2.67-2.87 (m, 4H), 2.21-2.35 (m, 1H), 1.90-2.19 (m, 6H), 1.75-1.87 (m, 1H), 1.29-1.38 (m, 6H).

ESI-MS: 783 (M+1)$^+$.

The compound 4r has been prepared according to the method described for the compound 4b by reducing compound 3r (782 mg, 1.0 mmol) using SnCl$_2$.2H$_2$O (1.125 g, 5.0 mmol) to afford compound 4r (730 mg, 95%), which was directly used in the next step.

The compound 5r was prepared according to the method described for the compound 5b employing the compound 4r (752 mg, 1.0 mmol) and HgCl$_2$ (544 mg, 2.0 mmol), CaCO$_3$ (200 mg, 2.0 mmol) to afford the compound 5r (314 mg, 50% yield).

$^1$H NMR (CDCl$_3$): δ 8.22-8.29 (m, 2H), 8.00 (d, 1H, J=8.3 Hz), 7.58-7.67 (m, 3H), 7.44-7.55 (m, 2H), 7.39 (t, 1H, J=7.5 Hz), 7.24-7.30 (m, 2H), 6.91-7.00 (m, 1H), 6.79-6.87 (m, 3H), 4.02-4.24 (m, 2H), 3.77-3.96 (m, 9H), 3.69-3.75 (m, 1H), 3.53-3.65 (m, 1H), 2.24-2.39 (m, 2H), 1.86-2.13 (m, 6H). ESI-MS: 629 (M+1)$^+$.

Biological Activity of C8-Linked Benzylidineanthracenone-PBD Hybrids

In Vitro Cytotoxicity

The C8-linked benzylidineanthracenone-PBD hybrids have been tested against eight human tumor cell lines derived from seven cancer types (breast, ovarian, colon, prostate, cervix, lung and oral cancer). For each compound, dose response curves for individual cell lines have been measured at a minimum of five concentrations at 10 fold dilutions. A protocol of 48 hrs continuous drug exposure has been used, and a sulforhodamine B (SRB) protein assay was used to estimate cell viability or growth. The results are expressed as percent of cell growth determined relative to that of untreated control cells. The GI$_{50}$ values are the concentration for 50% cell growth inhibition (GI$_{50}$) compared with the control has been calculated.

The compounds 5b 5c, 5d, 5h, 5m and 5r were evaluated for in vitro anticancer activity against eight human tumor cell lines derived from seven cancer types (breast, ovarian, colon, prostate, cervix, lung and oral cancer) as shown in Table 1.

The mean graph midpoint value of GI50 for compounds 5b 5c, 5d, 5h, 5m and 5r has been evaluated for different cancer cell lines and are listed in Table 1. All these six compounds showed good anti cancer activity against different cancer cell lines in the range of GI$_{50}$ values 0.9-2.5 μM concentration. Among them all compounds tested, compound 5c exhibited an interesting profile of activity and selectivity for various cancer cell lines as demonstrated by mean graph pattern.

TABLE 1

Cytotoxicity of compounds 5b, 5c, 5d, 5h, 5m and 5r in selected cancer cell lines

| Cancer panel/ cell line | GI$_{50}$ (μM) | | | | | | |
|---|---|---|---|---|---|---|---|
| | 5b | 5c | 5d | 5h | 5m | 5r | DC-81 |
| Breast MCF7 | 0.14 | 0.09 | 0.15 | 0.16 | 0.17 | 0.18 | 2.19 |
| Ovarian A2780 | 0.148 | 0.15 | 0.15 | 0.168 | 0.16 | 0.166 | 0.15 |

TABLE 1-continued

Cytotoxicity of compounds 5b, 5c, 5d, 5h, 5m and 5r in selected cancer cell lines

| Cancer panel/ cell line | GI$_{50}$ (μM) | | | | | | |
|---|---|---|---|---|---|---|---|
| | 5b | 5c | 5d | 5h | 5m | 5r | DC-81 |
| Colon Colo205 | 0.11 | 0.12 | — | 0.11 | 0.14 | 0.14 | 0.12 |
| Prostate PC-3 | 0.18 | 0.18 | 0.15 | 2.2 | 0.18 | 2.1 | 0.20 |
| Cervix SiHa | 2.2 | — | 2.2 | 2.5 | 2.2 | 31 | 0.17 |
| Lung | | | | | | | |
| A-549 | 1.76 | 1.8 | 1.94 | 0.15 | 1.82 | 1.9 | 0.38 |
| Hop62 | 0.19 | 0.18 | 0.17 | 0.2 | 0.23 | 0.26 | 0.15 |
| Oral KB | 0.19 | 0.20 | 0.18 | 2.4 | 2.4 | 2.5 | 0.20 |

Thermal Denaturation Studies

Compounds were subjected to thermal denaturation studies with duplex-form calf thymus DNA (CT-DNA) using an adaptation of a reported procedure. Working solutions in aqueous buffer (10 mM NaH$_2$PO$_{41}$Na$_2$HPO$_4$, 1 mM Na$_2$EDTA, pH 7.00±0.01) containing CT-DNA (100 μm in phosphate) and the PBD (20 μm) were prepared by addition of concentrated PBD solutions in DMSO to obtain a fixed [PBD]/[DNA] molar ratio of 1:5. The DNA-PBD solutions were incubated at 37° C. for 0, 18, and 36 h prior to analysis. Samples were monitored at 260 nm using a Beckman DU-7400 spectrophotometer fitted with high performance temperature controller, and heating was applied at 1° C. min$^{-1}$ in the 40-90° C. range. DNA helix→coil transition temperatures (Tm) were obtained from the maxima in the d(A$_{260}$)/dT derivative plots. Results are given as the mean±standard deviation from three determinations and are corrected for the effects of DMSO co-solvent using a linear correction term. Drug-induced alterations in DNA melting behaviour are given by: ΔTm=Tm(DNA+PBD)−Tm (DNA alone), where the Tm value for the PBD-free CT-DNA is 69.0±0.01. The fixed [PBD]/[DNA] ratio used did not result in binding saturation of the host DNA duplex for any compound examined. Compound 5b, 5c, 5d, 5h, 5m and 5r at 0 hr and 18 hr gradually increased at 37° C.

TABLE 2

Thermal denaturation data of C8-linked benzylidineanthracenone hybrids of pyrrolo[2,1-c][1,4]benzodiazepine with calf thymus (CT) DNA

| PBD hybrids | [PBD]:[DNA] molar ratio$^b$ | $T_m$° C.)$^a$ after incubation at 37° C. for | |
|---|---|---|---|
| | | 0 h | 18 h |
| 5b | 1:5 | 6.1 | 7.5 |
| 5c | 1:5 | 7.7 | 9.3 |
| 5d | 1:5 | 7.4 | 8.9 |
| 5h | 1:5 | 6.6 | 8.0 |
| 5m | 1:5 | 6.5 | 7.1 |
| 5r | 1:5 | 6.3 | 8.4 |
| DC-81 | 1:5 | 0.3 | 0.7 |
| 2a | 1:5 | 0.4 | 0.8 |
| 2b | 1:5 | 0.2 | 0.3 |
| 2c | 1:5 | 0.1 | 0.3 |
| 2d | 1:5 | 0.2 | 0.4 |

$^a$For CT-DNA alone at pH 7.00±0.01, $T_m$=68.5° C.±0.01 (mean value from 10 separate determinations), all ΔT$_m$ values are ±0.1-0.2° C. For a 1:5 molar ratio of [PBD]/[DNA], where CT-DNA concentration=100 μM and ligand concentration=20 μM in aqueous sodium phosphate buffer [10 mM sodium phosphate+1 mM EDTA, pH 7.00±0.01]. The $\Delta T_m$ for PBD hybrids 5b, 5c, 5d, 5h, 5m and 5r at a [PBD]:[DNA] molar ratio of 1:5 increased to a value of 7.5° C., 9.3° C., 8.9° C., 8.0° C., 7.1° C., and 8.4° C. after 18 h incubation respectively.

The DNA binding activity for these novel C8-linked benzylidineanthracenone-PBD hybrids 5b, 5c, 5d, 5h, 5m and 5r has been examined by thermal denaturation studies using calf thymus (CT) DNA at 0 hr and 18 hr gradually increased at 37° C. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. Interestingly, in this assay one of the benzylidineanthracenone-PBD hybrids elevates the helix melting temperature of CT-DNA by a margin of 9.3° C. after incubation for 18 h at 37° C. Data for these hybrids and DC-81 are included in Table 2 for comparison.

ADVANTAGES OF THE INVENTION

1. The present invention provides a pyrrolo[2,1-c][1,4] benzodiazepine hybrids useful as antitumour agents.
2. It also provides a process for the preparation of novel pyrrolo[2,1-c][1,4]benzodiazepine hybrids.

We claim:
1. A compound of formula 5

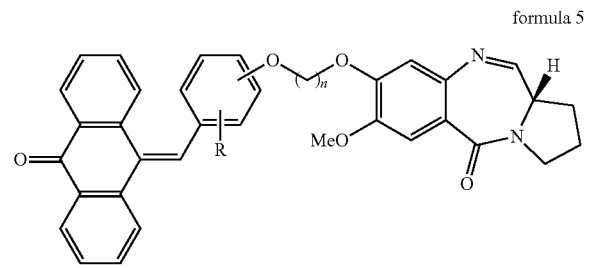

formula 5 wherein R=H or OCH$_3$; and n=2-6.

2. The compound according to claim 1 selected from the group consisting of:

7-methoxy-8-(2-{2-methoxy-4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one;

7-methoxy-8-(3-{2-methoxy-4-[(10-oxo-9,10-dihydro-9-anthracenyliden)methyl]ph enoxy}propoxy)-(11aS)-1,2,3,11a-5H-pyrrolo[2,1-c][1,4]-benzodiazepin-5-one;

7-methoxy-8-(4-{2-methoxy-4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one;

7-methoxy-8-(5-{2-methoxy-4-[(10-oxo-9,10-dihydro-9-anthracenyliden)methyl]ph enoxy}pentoxy)-(11aS)-1,2,3,11a-5H-pyrrolo[2,1-c][1,4]benzodiazepin-5-one;

7-methoxy-8-(6-{2-methoxy-4-[(10-oxo-9,10-dihydro-9-anthracenyliden)methyl]ph enoxy}hexoxy)-(11aS)-1,2,3,11a-5H-pyrrolo[2,1-c][1,4]benzodiazepin-5-one;

7-methoxy-8-(2-{4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one;

7-methoxy-8-(3-{-4[(10-oxo-9,10-dihydro-9-anthracenyliden)methyl]phenoxy}propoxy)-(11aS)-1,2,3,11a-5H-pyrrolo[2,1-c][1,4]benzodiazepin-5-one;

7-methoxy-8-(4-{4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one;

7-methoxy-8-(5-{4-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one;

7-methoxy-8-(6-{4-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one;

7-methoxy-8-(2-{3-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one;

7-methoxy-8-(3-{3-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one;

7-methoxy-8-(4-{3-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one;

7-methoxy-8-(5-{3-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one; 7-methoxy-8-(6-{3-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one;

7-methoxy-8-(2-{2-methoxy-5-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one;

7-methoxy-8-(3-{2-methoxy-5-[(10-oxo-9,10-dihydro-9-anthracenyliden)methyl]ph enoxy}propoxy)-(11aS)-1,2,3,11a-5H-pyrrolo[2,1-c][1,4]benzodiazepin-5-one;

7-methoxy-8-(4-{2-methoxy-5-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one;

7-methoxy-8-(5-{2-methoxy-5-[(10-oxo-9,10-dihydro-9-anthracenyliden)methyl]ph enoxy}pentoxy)(11aS)-1,2,3,11a-5H-pyrrolo[2,1-c][1,4]benzodiazepin-5-one; and 7-methoxy-8-(6-{2-methoxy-5-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one.

3. A process for the preparation of a compound of formula 5

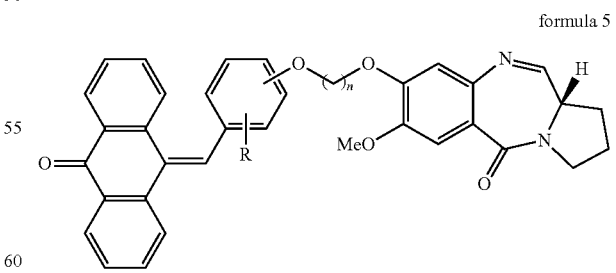

formula 5 wherein R=H or OCH$_3$, and n=2-6, wherein the process comprises the steps of:

a) reacting(2S)-N-[4-(n-bromoalkyl)oxy-5-methoxy-2-nitrobenzoyl]pyrrolidine-2-carboxaldehyde diethylthioacetal of formula 1a-e;

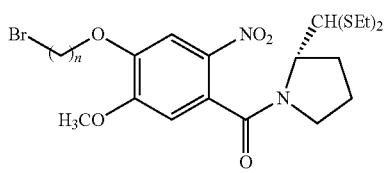

1a-e 1a n = 2
1b n = 3
1c n = 4
1d n = 5
1e n = 6 with a hydroxy substituted benzylidineanthracenone derivative selected from compounds of formula 2a-d

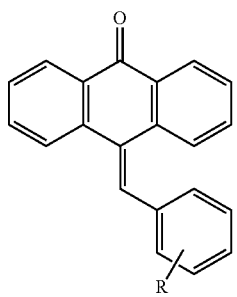

2a-d

2a R = 3-OMe, 4-OH
2b R = 4-OH
2c R = 3-OH
2d R = 4-OMe, 3-OH in the presence of inorganic base, in an organic solvent, at a temperature in the range of 55 to 60° C. to obtain the resultant nitro compound of formula 3a-t;

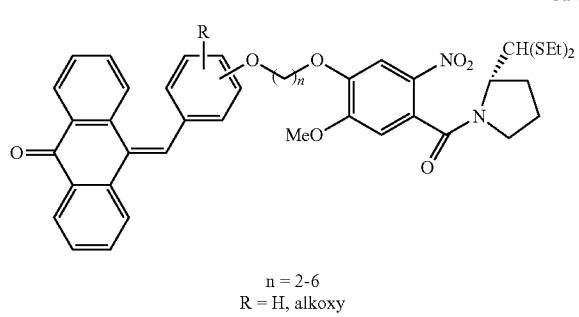

3a-t n = 2-6
R = H, alkoxy b) reducing said nitro compound of formula 3a-t with SnCl$_2$.2H$_2$O, in an alcohol, under reflux, followed by the evaporation of alcohol and basifying with a base, followed by extraction with ethyl acetate and washing the combined organic phase with brine solution and evaporating the solvent to obtain an amino compound of formula 4a-t;

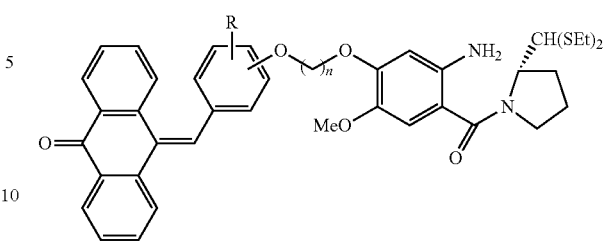

4a-t n = 2-6
R = H, alkoxy c) reacting said amino compound of formula 4a-t with deprotecting agent, mercuric chloride, in a mixture of water and organic solvent, in the presence of base, under stirring at a temperature in the range of 20-30° C., for a period in the range of 8-12 hrs, followed by filtration, extraction and washing with sodium bicarbonate and brine solution respectively;

d) evaporating the organic layer under reduced pressure; and e) purifying by column chromatography to obtain a compound of formula 5.

4. The process according to claim 3, wherein the inorganic base used in step (a) is selected from potassium carbonate or sodium carbonate.

5. The process according to claim 3, wherein the base used in step (b) is sodium carbonate.

6. The process according to claim 3, wherein the base used in step (c) is calcium carbonate.

7. The process according to claim 3, wherein the organic solvent used in step (a) is selected from the group consisting of acetone, N,N-dimethylformamide and acetonitrile.

8. The process according to claim 3, wherein the alcohol used in step (b) is selected from the group consisting of methanol, ethanol and isopropanol.

9. The process according to claim 3, wherein the organic solvent used in step (c) is selected from the group consisting of acetone, acetonitrile, chloroform, dichloromethane and tetrahydrofuran.

10. A method for inhibiting the growth of cancer cells derived from cancer cell lines, comprising contacting cancer cells selected from the group consisting of lung, cervix, ovarian, breast, colon, prostate and oral cells, with a compound of formula 5

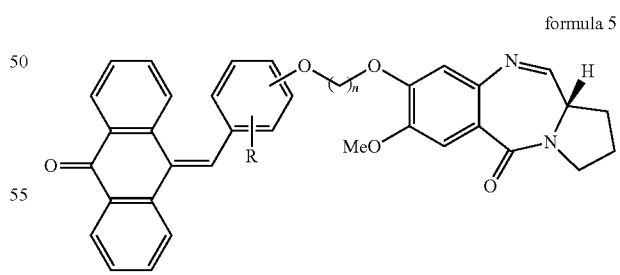

formula 5:
wherein R═H or OCH$_3$; and n=2-6.

11. The method according to claim 10, wherein the compound is selected from the group consisting of:
7-methoxy-8-(2-{2-methoxy-4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5a);

7-methoxy-8-(3-{2-methoxy-4-[(10-oxo-9,10-dihydro-9-anthracenyliden)methyl]ph enoxy}propoxy)-(11aS)-1,2,3,11a-5H-pyrrolo[2,1-c][1,4]-benzodiazepin-5-one (5b);

7-methoxy-8-(4-{2-methoxy-4-[(10-oxo-9,10-dihydro-9-anthracenyliden)methyl]phenoxy}butoxy)-(11aS)-1,2,3,11a-5H-pyrrolo[2,1-c][1,4]-benzodiazepin-5-one (5c);

7-methoxy-8-(5-{2-methoxy-4-[(10-oxo-9,10-dihydro-9-anthracenyliden)methyl]ph enoxy}pentoxy)-(11aS)-1,2,3,11a-5H-pyrrolo[2,1-c][1,4]benzodiazepin-5-one (5d);

7-methoxy-8-(6-{2-methoxy-4-[(10-oxo-9,10-dihydro-9-anthracenyliden)methyl]ph enoxy}hexoxy)-(11aS)-1,2,3,11a-5H-pyrrolo[2,1-c][1,4]benzodiazepin-5-one (5e);

7-methoxy-8-(2-{4-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5f);

7-methoxy-8-(3-{4-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5g);

7-methoxy-8-(4-{4-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5h);

7-methoxy-8-(5-{4-[(10-oxo-9,10-dihydro-9-anthracenyliden)methyl]phenoxy}pentoxy)-(11aS)-1,2,3,11a-5H-pyrrolo[2,1-c][1,4]benzodiazepin-5-one (5i);

7-methoxy-8-(6-{4-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5j);

7-methoxy-8-(2-{3-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5k);

7-methoxy-8-(3-{3-[(10-oxo-9,10-dihydro-9-anthracenyliden)methyl]phenoxy}propoxy)-(11aS)-1,2,3,11a-5H-pyrrolo[2,1-c][1,4]benzodiazepin-5-one (5l);

7-methoxy-8-(4-{3-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5m);

7-methoxy-8-(5-{3[(10-oxo-9,10-dihydro-9-anthracenyliden)methyl]phenoxy}pentoxy)-(11aS)-1,2,3,11a-5H-pyrrolo[2,1-c][1,4]-benzodiazepin-5-one (5n);

7-methoxy-8-(6-{3-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5o);

7-methoxy-8-(2-{2-methoxy-5-[(10-oxo-9,10-dihydro-9-anthracenyliden)methyl]phenoxy}ethoxy)-(11aS)-1,2,3,11a-5H-pyrrolo[2,1-c][1,4]benzodiazepin-5-one (5p);

7-methoxy-8-(3-{2-methoxy-5-[(10-oxo-9,10-dihydro-9-anthracenyliden)methyl]ph enoxy}propoxy)-(11aS)-1,2,3,11a-5H-pyrrolo[2,1-c][1,4]benzodiazepin-5-one (5q);

7-methoxy-8-(4-{2-methoxy-5-[(10-oxo-9,10-dihydro-9-anthracenyliden)methyl]phenoxy}butoxy)-(11aS)-1,2,3,11a-5H-pyrrolo[2,1-c][1,4]benzodiazepin-5-one (5r);

7-methoxy-8-(5-{2-methoxy-5-[(10-oxo-9,10-dihydro-9-anthracenyliden)methyl]ph enoxy}pentoxy)(11aS)-1,2,3,11a-5H-pyrrolo[2,1-c][1,4]benzodiazepin-5-one (5s); and 7-methoxy-8-(6-{2-methoxy-5-[(10-oxo-9,10-dihydro-9-anthracenyliden)methyl]phenoxy}hexoxy)-(11aS)-1,2,3,11a-5H-pyrrolo[2,1-c][1,4]benzodiazepin-5-one (5t).

12. The method according to claim 11, wherein the concentration of the compounds 5b, 5c, 5h, 5m or 5r used against colon cancer cell lines (Colo205) for $GI_{50}$ is in the range of 0.11 to 0.14 μm at an exposure period of at least 48 hours.

13. The method according to claim 11, wherein the concentration of the compounds 5b, 5c, 5d, 5h, 5m or 5r used against breast cancer cell lines (MCF7) for $GI_{50}$ is in the range of 0.09-0.18 μm at an exposure period of at least 48 hours.

14. The method according to claim 11, wherein the concentration of the compounds 5b, 5c, 5d, 5h, 5m or 5r used against prostate cancer cell lines (PC3) for $GI_{50}$ is in the range of 0.15-2.2 μm at an exposure period of at least 48 hours.

15. The method according to claim 11, wherein the concentration of the compounds 5b, 5d, 5h, 5m or 5r used against cervix cancer cell lines (SiHa) for $GI_{50}$ is in the range of 2.2-31 μm at an exposure period of at least 48 hours.

16. The method according to claim 11, wherein the concentration of the compounds 5b, 5c, 5d, 5h, 5m or 5r used against ovarian cancer cell lines (A2780) for $GI_{50}$ is in the range of 0.148-0.168 μm at an exposure period of at least 48 hours.

17. The method according to claim 11, wherein the concentration of the compounds 5b, 5c, 5d, 5h, 5m or 5r used against lung cancer cell lines (A549) for $GI_{50}$ is in the range of 0.155-1.94 μm at an exposure period of at least 48 hours.

18. The method according to claim 11, wherein the concentration of the compounds 5b, 5c, 5d, 5h, 5m or 5r used against lung cancer cell lines (HoP62) for $GI_{50}$ is in the range of 0.17-0.26 μm at an exposure period of at least 48 hours.

19. The method according to claim 11, wherein the concentration of the compounds 5b, 5c, 5d, 5h, 5m or 5r used against oral cancer cell lines (KB) for $GI_{50}$ is in the range of 0.18-2.5 μm at an exposure period of at least 48 hours.

* * * * *